United States Patent
Xie et al.

(10) Patent No.: US 10,568,494 B2
(45) Date of Patent: Feb. 25, 2020

(54) TERAHERTZ ENDOSCOPE SUITABLE FOR INTESTINAL TRACT LESION INSPECTION AND INSPECTION METHOD THEREOF

(71) Applicant: ZHEJIANG UNIVERSITY, Hangzhou, Zhejiang (CN)

(72) Inventors: Lijuan Xie, Zhejiang (CN); Chen Wang, Zhejiang (CN); Yibin Ying, Zhejiang (CN); Aichen Wang, Zhejiang (CN); Yuxin Huang, Zhejiang (CN)

(73) Assignee: ZHEJIANG UNIVERSITY, Hangzhou, Zhejiang (CN)

( * ) Notice: Subject to any disclaimer, the term of this patent is extended or adjusted under 35 U.S.C. 154(b) by 0 days.

(21) Appl. No.: 15/774,584

(22) PCT Filed: Apr. 16, 2016

(86) PCT No.: PCT/CN2016/079521
§ 371 (c)(1),
(2) Date: May 8, 2018

(87) PCT Pub. No.: WO2017/177469
PCT Pub. Date: Oct. 19, 2017

(65) Prior Publication Data
US 2018/0325366 A1 Nov. 15, 2018

(51) Int. Cl.
*A61B 1/018* (2006.01)
*A61B 5/00* (2006.01)
(Continued)

(52) U.S. Cl.
CPC ......... *A61B 1/018* (2013.01); *G01N 21/3581* (2013.01); *G01N 21/39* (2013.01);
(Continued)

(58) Field of Classification Search
CPC .. A61B 1/018; A61B 1/06; A61B 1/07; A61B 1/00027; A61B 1/00018;
(Continued)

(56) References Cited

U.S. PATENT DOCUMENTS 5,711,756 A * 1/1998 Chikama ............ A61B 1/00096
600/112
9,203,136 B2 * 12/2015 Huang ..................... H01Q 1/00
(Continued)

FOREIGN PATENT DOCUMENTS

| | | |
|---|---|---|
| CN | 204495714 U | 7/2015 |
| JP | 2005261826 A | 9/2005 |

(Continued)

*Primary Examiner* — Timothy J Neal
*Assistant Examiner* — William B Chou

(57) ABSTRACT

A terahertz endoscope suitable for intestinal tract lesion inspection and an inspection method are provided. The terahertz endoscope includes a combined tube body inserted into an intestinal tract, a terahertz signal enhancement module, a terahertz inspection module, and a real-time imaging module. The combined tube body mainly includes a sleeve tube (6), a sleeve head (7) and a hemispherical glass cover (8). The terahertz signal enhancement module mainly includes a tunable laser (2) and an optical fiber (9) installed in the sleeve tube (6). The terahertz inspection module mainly includes a terahertz wave detector (4), a terahertz wave transmitter (5), as well as a first stainless steel metal wire (12) and a second stainless steel metal wire (13) installed in the combined tube body.

13 Claims, 4 Drawing Sheets

(51) Int. Cl.
  *A61B 1/06* (2006.01)
  *A61B 1/05* (2006.01)
  *G01N 21/3581* (2014.01)
  *G01N 21/39* (2006.01)
  *G01N 21/552* (2014.01)

(52) U.S. Cl.
  CPC .............. *A61B 1/05* (2013.01); *A61B 1/0676* (2013.01); *A61B 1/0684* (2013.01); *A61B 5/0086* (2013.01); *A61B 5/4255* (2013.01); *A61B 5/6847* (2013.01); *G01N 21/554* (2013.01)

(58) Field of Classification Search
  CPC ........... A61B 5/05; A61B 5/0507; A61B 5/00; G01N 21/3581; G02B 23/24; G02B 23/2484
  See application file for complete search history.

(56) References Cited

U.S. PATENT DOCUMENTS

| | | | | |
|---|---|---|---|---|
| 9,341,567 B2* | 5/2016 | Nakayama | ............. | B82Y 20/00 |
| 9,813,165 B2* | 11/2017 | Clerici | ................... | H04B 10/90 |
| 10,088,415 B2* | 10/2018 | Ataka | ................. | G01N 21/3581 |
| 2008/0309577 A1* | 12/2008 | Mittleman | ......... | G01N 21/3581 |
| | | | | 343/850 |
| 2009/0287091 A1 | 11/2009 | Son | | |
| 2017/0059848 A1* | 3/2017 | Haraguchi | ........... | G02B 23/243 |
| 2017/0146453 A1* | 5/2017 | Giles | .................. | G01N 21/3581 |

FOREIGN PATENT DOCUMENTS

| | | |
|---|---|---|
| JP | 200846574 A | 2/2008 |
| WO | 2016022757 | 2/2016 |

* cited by examiner

TERAHERTZ ENDOSCOPE SUITABLE FOR INTESTINAL TRACT LESION INSPECTION AND INSPECTION METHOD THEREOF

CROSS REFERENCE OF RELATED APPLICATION

This is a U.S. National Stage under 35 U.S.C 371 of the International Application PCT/CN2015/079521, filed Apr. 16, 2016.

BACKGROUND OF THE PRESENT INVENTION

Field of Invention

The present invention relates to the field of Terahertz technology for detection, to and more particularly to a terahertz endoscope suitable for intestinal tract lesion inspection and inspection method thereof.

Description of Related Arts

In medical testing, the earlier the lesion is found, the lower difficulty and the less costly it is to cure. For example, cancer, early detection and timely treatment are important for curing cancer and preventing some diseases from developing into cancer. Medical endoscope plays an important role in clinical testing, which is mainly used for the detection of early lesions in the intestine. The endoscope can pass through the natural orifice or a small incision of an organism to enter into the body of the test object and find the lesions which cannot be displayed by the X-ray, so as to achieve the objects of early detection, early detection, early control and early treatment.

The conventional medical endoscopes for detecting intestinal tract lesions are mainly based on optical or acoustic imaging methods to obtain optical image information or acoustic image information in the intestine. Although the optical imaging based method can clearly obtain the external morphology of the intestinal inner wall, only some obvious surface lesions can be detected with low sensitivity. Although the method based on acoustic imaging can image the intestinal subwall tissue, but tiny lesions it cannot be screened out and the image resolution is low, too. Therefore, the development of a new type of endoscope for intestinal lesions timely and accurate detection is of great significance.

Terahertz radiation refers to a band of electromagnetic wave ranging from 0.1 THz to 10 THz which is in the transition from macro-electronics to micro-photonics and has many unique advantages. Terahertz radiation has low photon energy and is sensitive to water. The transitions between the vibrational levels and the transitions between rotational energies of many biological macromolecules lie in the terahertz region, and the diseased cells are metabolized more vigorously and contain more free water, so terahertz detection-based method has great potential in medical testing.

SUMMARY OF THE PRESENT INVENTION

In order to overcome the shortcomings in the conventional arts, the present invention provides a terahertz endoscope suitable for intestinal tract lesion inspection and inspection method, which can timely and accurately detect the intestinal wall lesions with characteristics of high sensitivity and compact structure, convenient operation and wide applicable range.

The technical solution adopted by the present invention is as follows.

1. A terahertz endoscope for intestinal tract lesion inspection, comprises:

a combined tube body comprising: a sleeve tube, a sleeve head and a hemispherical glass cover which are fixedly and axially connected in turn, wherein the combined tube body forms an external shell for inserting in intestinal tract;

a terahertz signal enhancement module comprising: a tunable laser and an optical fiber provided in the sleeve tube; wherein tunable laser is configured to generate a wavelength tunable laser beam, wherein the wavelength tunable laser beam is conducted to the sleeve head via the optical fiber and irradiated toward an internal wall of the intestinal tract to be tested for enhancing a terahertz signal reflected by the internal wall of the intestinal tract;

a terahertz detection module comprising: a terahertz wave detector, a terahertz wave transmitter, and a first stainless steel wire and a second stainless steel wire which are both provided in the combined tube body; wherein the terahertz wave transmitter is configured to generate terahertz wave, wherein the terahertz wave is transmitted by the first stainless steel wire and then emitted from the sleeve head towards the internal wall of the intestinal tract, the terahertz wave detector through a second stainless steel wire to obtain a terahertz echo signal carrying information of internal wall tissue of the intestinal tract to be tested;

a real-time imaging module comprising: an image processing and transmitting circuit board, and a power line, a video signal line, a cold LED light source and a CMOS camera which are provided in the combined tube body; wherein the image processing and transmitting circuit board are configured to control the cold LED light source to emit light to provide a light source for collecting image in the intestinal tract and meanwhile control the CMOS camera to shoot for obtaining a real-time image; the real-time image is transmitted by the CMOS camera via the video signal line; wherein the CMOS camera and the cold LED light source are connected with a power source via the power line.

Preferably, the first stainless steel wire, the second stainless steel wire, the power line, the video signal line and the optical fiber are all provided in the sleeve tube; an detection window is provided on a side wall of the sleeve head, a reflector is provided in the sleeve head; front end portions of the first stainless steel wire, the second stainless steel wire and the optical fiber all extends to the reflector; terahertz wave emitted by the first stainless steel wire and laser beam emitted by the optical fiber are reflected by the reflector and then transmitted through the detection window to reach the internal wall of the intestinal tract to be tested, an echo of the terahertz wave passes through the detection window and the reflector to be reflected back to a front portion of the second stainless steel wire to be received.

Preferably, the cold LED light source and the CMOS camera are both fixed in the hemispherical glass cover on an end portion of the sleeve head; front end portions of the power line and the video signal line pass through the reflector and are connected with the cold LED light source in the hemispherical glass cover and the CMOS camera.

Preferably, the optical fiber is sleeved in a middle portion of the sleeve tube, the first stainless steel wire and the second stainless steel wire are provided between an internal wall of the sleeve tube closer to a first side of the detection window and the optical fiber; the power line and the video signal line are provided between a second side of the internal wall of the sleeve tube further from the detection window and the optical fiber.

The terahertz endoscope for intestinal tract lesion inspection further comprises a computer, wherein the terahertz detection module and the real-time imaging module are both connected to the computer.

Preferably, the reflector is tilted at an angle of 45° with an axis of the sleeve head and fixed in the sleeve head; a reflecting surface of the reflector faces a rear end of the sleeve tube and the detection window, so as to convert a transmitting direction of the laser beam and the terahertz wave from a direction along an axis of the combine tube body to a direction perpendicular to the axis of the combine tube body.

Preferably, two through holes for passing through the power line and the video signal line are opened on a periphery of the second side further from the detection window.

Preferably, a front end portion of the first stainless steel line is contacted with a front end portion of the second stainless steel line; and other parts of the first stainless steel line and the second stainless steel line are separated.

Preferably, a distance along an axis direction between the front end portion of the first stainless steel line and the front end portion of the second stainless steel line is within 20 mm.

Preferably, a material of the detection window is TPX.

Preferably, the tunable laser is configured to adjust a wavelength according to detection requirements, so as to match a wavelength of a laser emitted with detection requirements.

2. A method for inspecting intestinal tract lesion utilizing the terahertz endoscope, comprises steps of:

S1: injecting a safe dose of gold nanorods solution into a subject to be detected;

S2: inserting the combined tube body into the intestinal tract, irradiating with the cold LED light source, obtaining an image of an internal portion of the intestinal tract in real time by a CMOS camera for determining a position of the sleeve head, and aligning the detection window of the sleeve head to the internal wall of the intestinal tract to be detected;

S3: gradually turning on the tunable laser, the terahertz transmitter and the terahertz detector; wherein the terahertz wave transmitter generates a terahertz wave to pass through the front end portion of the first stainless steel wire to emit to the internal wall of the intestinal tract to be detected; wherein the terahertz wave passes through the gold nanorods solution in the intestinal tract to be detected and is reflected, and received by the front end of the second stainless steel line to obtain the terahertz echo signal carrying information of the internal wall tissue of the intestinal tract to be detected;

S4: analyzing the terahertz echo signal received and the image in real time by the CMOS camera to obtain a result of lesion at a site of the internal wall of the intestinal tract to be detected;

S5: moving the sleeve head to align the detection window to a next detection portion for detecting.

Preferably, the step S3 further comprises a step of emitting laser irradiation by the tunable laser for auxiliary signal amplification of the reflected terahertz wave.

Preferably, during detection, the tunable laser performs adjusts wavelength according to an aspect ratio of gold nanorods in the gold nanorod solution, so as to match to laser wavelength emitted with the longitudinal surface plasmon resonance absorption peak of the gold nanorods.

Beneficial effects of the present invention are as follows.

The invention adopts terahertz radiation as the main light source for detection, which can better reflect the changes of the internal components of intestinal tissue cells and accurately detect the intestinal diseases in the early stage. The use of terahertz wave transmitter with adjustable wavelength makes it possible to acquire the terahertz information of intestinal tissue at different frequencies and obtain more abundant and comprehensive information to facilitate more detailed analysis on the intestinal tissue lesions, which provides a scientific and reliable basis for the choices of treatment programs. The present invention organically combines terahertz detection technology and medical diagnosis technology, expands the application range of terahertz technology and promotes the application of terahertz technology in the medical field.

At the same time, the fusion of terahertz information and visible light information in the intestine is analyzed to improve the accuracy of the detection. The surface plasmon resonance is induced by using the laser beam to enhance the sensitivity of the detection. The detection components entering the intestine are compact, with mall diameter, easy to operate.

The conventional endoscope is mainly based on optical or acoustic methods for detection, wherein the ability to obtain information is limited, the detection sensitivity is low, and subtle lesions cannot be detected accurately in real time. The endoscope of the present invention solves the above problems, and can accurately detect intestinal tract diseases in early stage and provide more information about the cytopathic effect of the cells. Fusion of terahertz information and visible light information in the intestine is analyzed, so as to improve the accuracy of detection. The tunable laser is used to excite gold nanorods to generate surface plasmon resonance to improve the detection sensitivity. The present invention has the advantages of compact structure, accurate and abundant signals obtained, convenient operation, and wide applicability.

Reference numbers in the Figures, 1—computer; 2—tunable laser; 3—image processing and transmitting circuit board; 4—terahertz wave detector; 5—terahertz wave transmitter; 6—sleeve tube; 7—sleeve head; 8—hemispherical glass cover; 9—optical fiber; 10—power line; 11—video signal line; 12—first stainless steel wire; 13—second stainless steel wire; 14—cold LED light source; 15—CMOS camera; 16—reflector; 17—detection window.

DETAILED DESCRIPTION OF THE PREFERRED EMBODIMENT

Further description of the present invention is illustrated combining with the accompanying drawings and the preferred embodiments of the present invention.

The present invention will be further described below by taking mammals as an example in conjunction with the accompanying drawings. However, the present invention is not limited to the following preferred embodiments.

Figure 1:
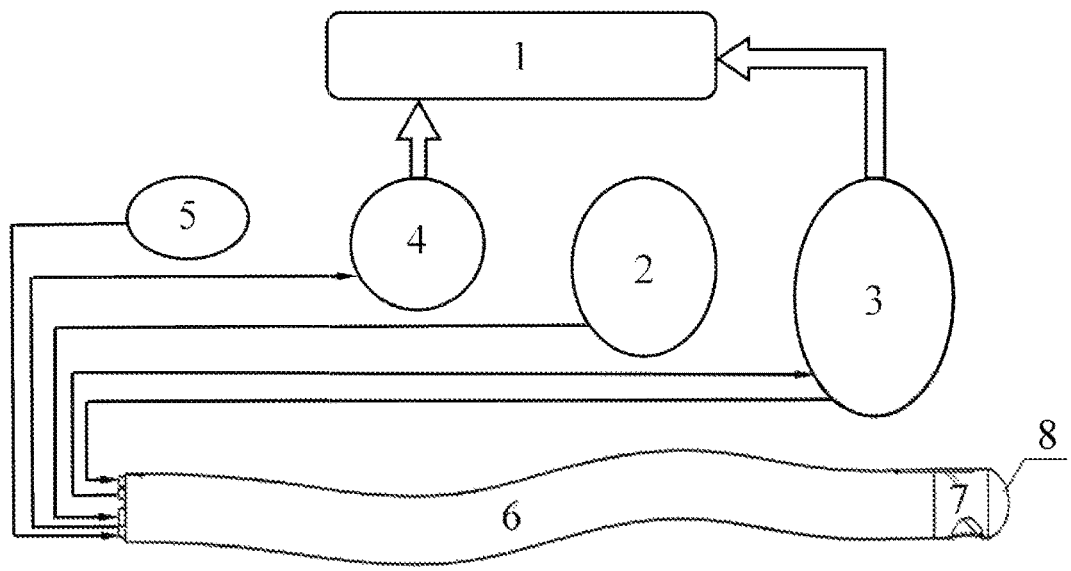
FIG. 1 is a schematic diagram of a connection structure of a terahertz endoscope according to a preferred embodiment of the present invention.

As shown in FIG. 1, the present invention comprises: a combined tube body, a terahertz signal enhancement module, a terahertz detection module and a real-time imaging module.

As shown in FIG. 1, the combined tube body comprises a sleeve tube 6, a sleeve head 7 and a hemispherical glass cover 8 which are fixedly and axially connected in turn to form an external shell for inserting in intestinal tract. The combined tube body is capable of form external shells with different tube diameters; wherein the sleeve tube 6, the sleeve head 7 and the hemispherical glass cover 8 are connected and fixed by screws or snaps; and a whole shell is capable of bending properly.

Figure 2:
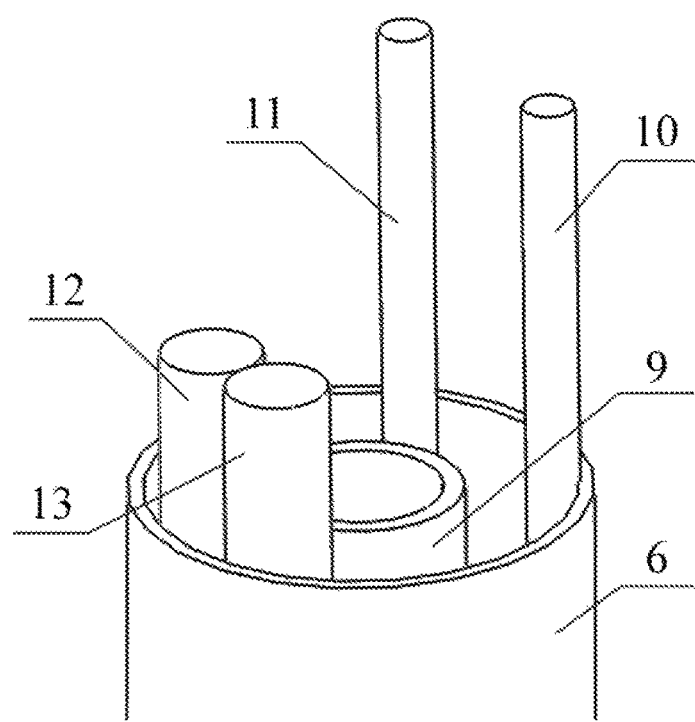
FIG. 2 is a stereo diagram of an end portion nearer to a sleeve head of the sleeve tube.
Figure 4:
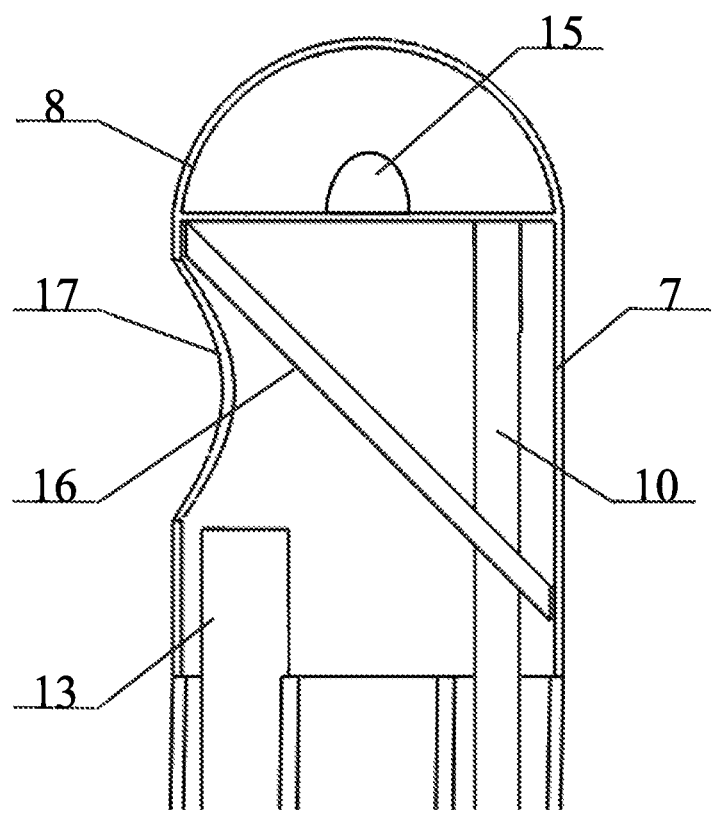
FIG. 4 is a sectional structure view of a junction of the sleeve tube and the sleeve head.

As shown in FIGS. 1, 2 and 4, the terahertz signal enhancement module comprises: a tunable laser 2 and an optical fiber 9 provided on an identical axis in the sleeve tube 6 to generate a wavelength tunable laser beam and transmit to an internal wall of the intestinal tract to be tested for enhancing a terahertz signal reflected by the internal wall of the intestinal tract.

As shown in FIGS. 1-4, the terahertz detection module comprises: a terahertz wave detector 4, a terahertz wave transmitter 5, and a first stainless steel wire 12 and a second stainless steel wire 13 which are provided between the sleeve tube 6 and the optical fiber 9; wherein the terahertz wave transmitter 5 is capable of adjusting frequency and intensity to generate terahertz signals with different frequencies and intensities at a range of 0.1 T-10 T. The terahertz wave transmitter 5 and the terahertz wave detector 4 are respectively connected with the first stainless steel wire 12 and the second stainless steel wire 13 for generating, transmitting and detecting terahertz wave.

Figure 5:
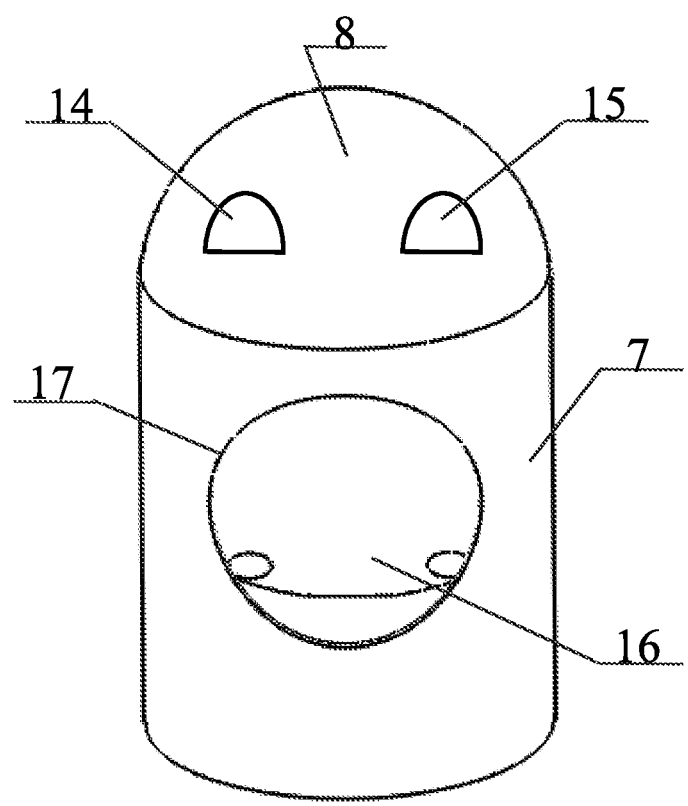
FIG. 5 is a stereo structure view of the sleeve head and a hemispherical glass cover.

As shown in FIGS. 1, 2 and 5, the real-time imaging module comprises an image processing and transmitting circuit board 3, and a power line 10 and a video signal line 11 which are both provided between the sleeve tube 6 and the optical fiber 9, a cold LED light source 14 and a CMOS camera 15 which are both fixed on an end portion of the sleeve head 7; wherein the image processing and transmitting circuit board 3 is respectively connected with the cold LED light source 14 and the CMOS (Complementary Metal Oxide Semiconductor) camera 15 via the power line 10 and the video signal line 11 Adopting miniature CMOS camera 15 is capable of not only ensuring the shooting quality but also reducing the volume of the sleeve head.

As shown in FIG. 4, the first stainless steel wire 12, the second stainless steel wire 13, the power line 10, the video signal line 11 and the optical fiber 9 are all provided in the sleeve tube 6; an detection window 17 with a diameter of 10 mm is provided on the sleeve head 7, wherein a material of the detection window 17 adopts TPX (methyl pentene copolymer); a reflector 16 is provided in the sleeve head 7, wherein the reflector 16 is tilted at an angle of 45° with an axis of the sleeve head 7 and fixed in the sleeve head 7; rear end portions of the first stainless steel wire 12, the second stainless steel wire 13 and the optical fiber 9 are respectively connected with the terahertz wave transmitter 5, the terahertz wave detector 4 and the tunable laser 2; the front end portions of the first stainless steel wire 12, the second stainless steel wire 13 and the optical fiber 9 all extends to the reflector 16; terahertz wave emitted by the first stainless steel wire 12 and laser beam emitted by the optical fiber 9 are reflected by the reflector 16 and then transmitted through the detection window 17 to reach the internal wall of the intestinal tract to be tested, an echo of the terahertz wave passes through the detection window 17 and the reflector 16 to be reflected back to a front portion of the second stainless steel wire 13 to be received.

The cold LED light source 14 and the CMOS camera 15 are both fixed in the hemispherical glass cover 8 on an end portion of the sleeve head 7; wherein rear end portions of the power line 10 and the video signal line 11 are respectively connected with the power source and the image processing and transmitting circuit board 3; front end portions of the power line 10 and the video signal line 11 pass through the reflector 16 to connect the cold LED light source 14 in the hemispherical glass cover 8 and the CMOS camera 15. Two through holes for passing through the power line 10 and the video signal line 11 are opened close to a periphery of the reflector 16.

Figure 3:
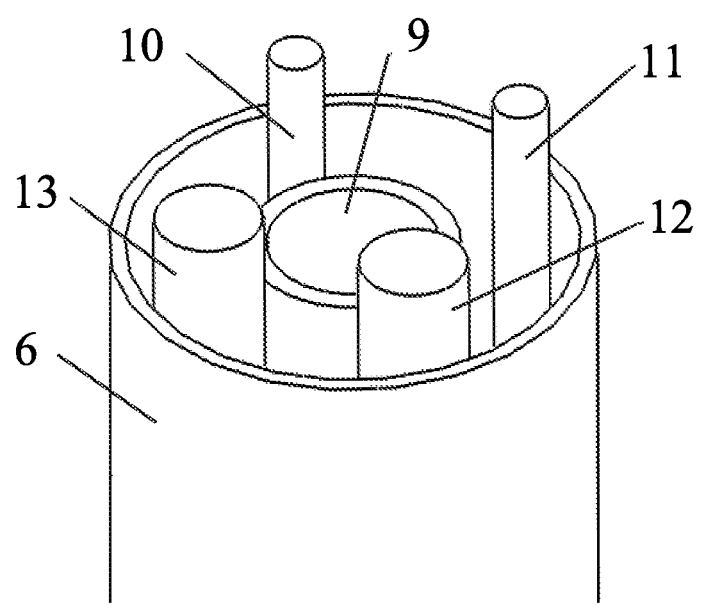
FIG. 3 is a stereo diagram of an end portion farther to the sleeve head of the sleeve tube.

As shown in FIGS. 2-4, the first stainless steel wire 12 and the second stainless steel wire 13 are only contacted with each other on ends close to the reflector 16 to enhance coupling effect; other positions of the first stainless steel wire 12 and the second stainless steel wire 13 are separated. The first stainless steel wire 12 and the second stainless steel wire 13 can be installed in parallel with distances, so as to reduce mutual interference therebetween. A distance along an axis direction between the front end portion of the first stainless steel line 12 and the front end portion of the second stainless steel line 13 is within 20 mm, so as to ensure the terahertz wave transmitted from the end portion of the first stainless steel line 12 can be incident on the reflector 16 in an original transmission direction.

As shown in FIG. 1, the computer 1 of the present invention is connected with both the terahertz wave detector 4 of the terahertz detection module and the image processing and transmitting circuit board 3 of the real-time imaging module for controlling.

Working principle of the inspection device of the present invention is illustrated with the FIG. 1 and FIG. 4.

The image processing and transmitting circuit board 3 controls the LED cold light source 14 to emit light through the power line 10 to provide a light source required for image acquisition in the intestine. Signals shot by the CMOS camera 15 are transmitted to the image processing and transmitting circuit board 3 via the video signal line 11, processed, and transmitted to the computer 1 to present the internal images of the intestine in real time. Approximate position of the sleeve head 7 is determined by the acquired image information, and the detection window 17 is adjusted to be aligned to a. portion to be detected. The tunable laser 2 adopts a dye laser, wherein an adjusting range of the wavelength is at a range of 300 nm-1200 nm, the laser beam emitted thereby attenuates, and then irradiates the site to be detected through the optical fiber 9 and the reflector 16 to facilitate enhancing reflected terahertz signals. The terahertz wave emitted by the terahertz wave emitter 5 pass through the first stainless steel wire 12 and the reflector 16 to be irradiated to the site to be detected. The reflected terahertz signal carrying information of the intestine wall tissue to be detected is transmitted to the is terahertz wave detector 4 through the reflector 16 and the second stainless steel wire 13, processed and transmitted to the computer 1 to display the terahertz information of a detected site. Through comprehensive analysis of the optical information and terahertz information, we can know whether there is lesion in the intestine wall tissue detected.

The preferred embodiments and the specific implementation process is illustrated in detail combining with the FIG. 1 and the FIG. 4.

S1: intravenously injecting antibody-modified gold nanorods solution with a concentration of about 3 mg/ml into animals to be tested, wherein the longitudinal plasmon resonance peak of the gold nanorods is located at 800 nm and such surface plasmon resonance can be generated irradiated by a laser beam of 800 nm; the gold nanorods injected can gather in target cells of the intestine through blood circulation;

S2: opening the computer 1 and the image processing and transmitting circuit board 3, wherein the combined tube body with a suitable tube diameter is selected according to sizes of the intestine to be detected; the combined tube body is inserted into the intestine of the animal; by controlling the LED cold light source 14 and the CMOS camera 15, internal image of the intestine is obtained and general location of the sleeve head 7 is determined;

S3: gradually turning on the tunable laser 2, the terahertz wave transmitter 5 and the terahertz detector 4, adjusting an emission wavelength of the tunable laser 2 to be 800 nm, aligning the detection window 17 to the test site in the intestine, obtaining the terahertz signal of the site, adjusting the transmitting frequency of the terahertz emitter according to requirements for various suspected intestinal diseases detection, so as to obtain the response signal of the site to be detected at different terahertz frequencies;

S4: analyzing the terahertz information of the intestine internal wall combining with the image information; wherein due to the differences in water content and inter-organizational structure between normal tissue cells and diseased tissue cells, these differences can be revealed in different terahertz bands, and taking advantage of the magnifying effect achieved by 800 nm infrared laser and the gold nanorods, whether there is any lesion in this part can be determined timely and accurately; the response signals of lesions with different terahertz frequencies is further analyzed, including parameters of absorbance and extinction coefficient, so as to diagnose what lesions occurs for giving a reasonable and targeted treatment program;

S5: moving the detection window 17 to detect a next test site.

It can be seen from the preferred embodiments that the present invention utilizes terahertz radiation as a detecting light source to accurately detect intestinal tract lesions in the early stage and can better reflect changes in the internal components of intestinal tissue cells with high accuracy and high sensitivity. The information obtained is richer and more comprehensive, which facilitates more detailed analysis of the intestinal tissue lesions, and the technical effect is remarkable.

One skilled in the art will understand that the embodiment of the present invention as shown in the drawings and described above is exemplary only and not intended to be limiting. It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A terahertz endoscope for intestinal tract lesion inspection, comprising:

a combined tube body comprising: a sleeve tube (6), a sleeve head (7) and a hemispherical glass cover (8) which are fixedly and axially connected in turn, wherein the combined tube body forms an external shell for inserting in intestinal tract;

a terahertz signal enhancement module comprising: a tunable laser (2) and an optical fiber (9) provided in the sleeve tube (6); wherein tunable laser (2) is configured to generate a wavelength tunable laser beam, wherein the wavelength tunable laser beam is conducted to the sleeve head (7) via the optical fiber (9) and irradiated toward an internal wall of the intestinal tract to be tested for enhancing a terahertz signal reflected by the internal wall of the intestinal tract;

a terahertz detection module comprising: a terahertz wave detector (4), a terahertz wave transmitter (5), and a first stainless steel wire (12) and a second stainless steel wire (13) which are both provided in the combined tube body; wherein the terahertz wave transmitter (5) is configured to generate terahertz wave, wherein the terahertz wave is transmitted by the first stainless steel wire (12) and then emitted from the sleeve head (7) towards the internal wall of the intestinal tract, so as to be received and detected by the terahertz wave detector (4) through a second stainless steel wire (13) carrying information of internal wall tissue of the intestinal tract to be tested;

a real-time imaging module comprising: an image processing and transmitting circuit board (3), and a power line (10), a video signal line (11), a cold LED light source (14) and a CMOS camera (15) which are provided in the combined tube body; wherein the image processing and transmitting circuit board (3) is configured to control the cold LED light source (14) to emit light to provide a light source for collecting image in the intestinal tract and meanwhile control the CMOS camera (15) to shoot for obtaining a real-time image; the real-time image is transmitted by the CMOS camera (15) via the video signal line (11); wherein the CMOS camera (15) and the cold LED light source (14) are connected with a power source via the power line (10);

wherein the first stainless steel wire (12), the second stainless steel wire (13), the power line (10), the video signal line (11) and the optical fiber (9) are all provided in the sleeve tube (6); a detection window (17) is provided on a side wall of the sleeve head (7), a reflector (16) is provided in the sleeve head (7); front-end portions of the first stainless steel wire (12), the second stainless steel wire (13) and the optical fiber (9) all extends to the reflector (16); terahertz wave emitted by the first stainless steel wire (12) and laser beam emitted by the optical fiber (9) are reflected by the reflector (16) and then transmitted through the detection window (17) to reach the internal wall of the intestinal tract to be tested, an echo of the terahertz wave passes through the detection window (17) and the reflector (16) to be reflected back to a front portion of the second stainless steel wire (13) to be received.

2. The terahertz endoscope for intestinal tract lesion inspection, as recited in claim 1, wherein the cold LED light source (14) and the CMOS camera (15) are both fixed in the hemispherical glass cover (8) on an end portion of the sleeve head (7); front-end portions of the power line (10) and the video signal line (11) pass through the reflector (16) to connect with the cold LED light source (14) in the hemispherical glass cover (8) and the CMOS camera (15).

3. The terahertz endoscope for intestinal tract lesion inspection, as recited in claim 1, wherein the optical fiber (9) is sleeved in a middle portion of the sleeve tube (6), the first stainless steel wire (12) and the second stainless steel wire

(13) are provided between an internal wall of the sleeve tube (6) closer to a first side of the detection window (17) and the optical fiber (9); the power line (10) and the video signal line (11) are provided between a second side of the internal wall of the sleeve tube (6) further from the detection window (17) and the optical fiber (9).

4. The terahertz endoscope for intestinal tract lesion inspection, as recited in claim 1, further comprising a computer (1), wherein the terahertz detection module and the real-time imaging module are both connected to the computer (1).

5. The terahertz endoscope for intestinal tract lesion inspection, as recited in claim 1, wherein the reflector (16) is tilted at an angle of 45° with an axis of the sleeve head (7) and fixed in the sleeve head (7); a reflecting surface of the reflector (16) faces a rear end of the sleeve tube (6) and the detection window (17), so as to convert a transmitting direction of the laser beam and the terahertz wave from a direction along an axis of the combined tube body to a direction perpendicular to the axis of the combine tube body.

6. The terahertz endoscope for intestinal tract lesion inspection, as recited in claim 1, wherein two through holes for passing through the power line (10) and the video signal line (11) are opened on a periphery of the second side further from the detection window (17).

7. The terahertz endoscope for intestinal tract lesion inspection, as recited in claim 1, wherein a front-end portion of the first stainless steel line (12) is contacted with a front-end portion of the second stainless steel line (13); and other parts of the first stainless steel line (12) and the second stainless steel line (13) are separated.

8. The terahertz endoscope for intestinal tract lesion inspection, as recited in claim 1, wherein a distance along an axis direction between the front-end portion of the first stainless steel line (12) and the front-end portion of the second stainless steel line (13) is within 20 mm.

9. The terahertz endoscope for intestinal tract lesion inspection, as recited in claim 1, wherein a material of the detection window (17) is TPX.

10. The terahertz endoscope for intestinal tract lesion inspection, as recited in claim 1, wherein the tunable laser (2) is configured to adjust a wavelength, so as to emit a wavelength of a laser matching with detection requirements.

11. A method for inspecting intestinal tract lesion utilizing the terahertz endoscope as recited in claim 1, comprising steps of:
S1: injecting a safe dose of gold nanorods solution into a subject to be detected;
S2: inserting the combined tube body into the intestinal tract, irradiating with the cold LED light source (14), obtaining an image of an internal portion of the intestinal tract in real time by a CMOS camera (15) for determining a position of the sleeve head (7), and aligning the detection window (17) of the sleeve head (7) to the internal wall of the intestinal tract to be detected;
S3: gradually turning on the tunable laser (2), the terahertz transmitter (5) and the terahertz detector (4); wherein the terahertz wave transmitter (5) generates a terahertz wave to pass through the front-end portion of the first stainless steel wire (12) to emit to the internal wall of the intestinal tract to be detected; wherein the terahertz wave passes through the gold nanorods solution in the intestinal tract to be detected and is reflected, and received by the front-end of the second stainless steel line (13) to obtain the terahertz echo signal carrying information of the internal wall tissue of the intestinal tract to be detected;
S4: analyzing the terahertz echo signal received and the image in real time collected by the CMOS camera (15) to obtain a result of lesion at a site of the internal wall of the intestinal tract to be detected;
S5: moving the sleeve head (7) to align the detection window (17) to a next detection portion for detecting.

12. The method for inspecting intestinal tract lesion, as recited in claim 11, wherein the step (S3) further comprises a step of emitting laser irradiation by the tunable laser (2) for auxiliary signal amplification of the reflected terahertz wave.

13. The method for inspecting intestinal tract lesion, as recited in claim 11, wherein during detection, the tunable laser (2) performs adjusts wavelength according to an aspect ratio of gold nanorods in the gold nanorods solution, so as to match laser wavelength emitted with a longitudinal surface plasmon resonance absorption peak of the gold nanorods.

* * * * *